(12) United States Patent
Soga et al.

(10) Patent No.: US 10,789,915 B2
(45) Date of Patent: Sep. 29, 2020

(54) ACOUSTIC STRING INSTRUMENT, AND METHODS FOR MANUFACTURING AND REPAIRING SAME

(71) Applicant: Yamaha Corporation, Hamamatsu, Shizuoka (JP)

(72) Inventors: Kazuki Soga, Shizuoka (JP); Toshihisa Yamazaki, Jakarta (ID); Yoshiro Yamauchi, Shizuoka (JP); Akio Matsushima, Shizuoka (JP); Hiroshi Nakaya, Shizuoka (JP)

(73) Assignee: YAMAHA CORPORATION, Shizuoka (JP)

( * ) Notice: Subject to any disclaimer, the term of this patent is extended or adjusted under 35 U.S.C. 154(b) by 0 days.

(21) Appl. No.: 16/510,227

(22) Filed: Jul. 12, 2019

(65) Prior Publication Data

US 2019/0333482 A1    Oct. 31, 2019

Related U.S. Application Data

(63) Continuation of application No. PCT/JP2017/001231, filed on Jan. 16, 2017.

(51) Int. Cl.
*G10D 3/22* (2020.01)
*G10D 1/02* (2006.01)

(52) U.S. Cl.
CPC ............. *G10D 3/22* (2020.02); *G10D 1/02* (2013.01)

(58) Field of Classification Search
CPC ............. G10D 1/005; G10D 1/02; G10D 3/22
See application file for complete search history.

(56) References Cited

U.S. PATENT DOCUMENTS

| 3,699,836 | A | * | 10/1972 | Glasser | G10D 1/005 84/291 |
| 4,304,164 | A | * | 12/1981 | Baker | G10D 1/02 84/274 |
| 4,367,777 | A | * | 1/1983 | Baker | G10D 1/02 144/346 |
| 4,977,808 | A | * | 12/1990 | Thacker | G10D 3/22 84/291 |
| 6,177,622 | B1 | * | 1/2001 | Green | G10D 1/02 84/274 |
| 8,940,984 | B2 | * | 1/2015 | Davies | G10D 1/02 84/280 |

(Continued)

FOREIGN PATENT DOCUMENTS

| JP | H08-185155 A | 7/1996 |
| JP | 2000-027316 A | 1/2000 |

(Continued)

OTHER PUBLICATIONS

International Search Report in PCT/JP2017/001231 dated Mar. 7, 2017.

*Primary Examiner* — Robert W Horn
(74) *Attorney, Agent, or Firm* — Global IP Counselors, LLP (57) ABSTRACT

An acoustic string instrument includes a top plate, a back plate, and a body disposed between the top plate and the back plate. The body has a plurality of first positioning portions. At least one of the top plate or the back plate, or both has a plurality of second positioning portions. The first positioning portions are fixed to the second positioning portions corresponding to the first positioning portions.

8 Claims, 10 Drawing Sheets

(56) References Cited

U.S. PATENT DOCUMENTS

| | | | | |
|---|---|---|---|---|
| 9,190,035 | B1* | 11/2015 | Ranck Fields | G10D 1/02 |
| 10,540,945 | B2* | 1/2020 | Upton | G10D 3/04 |
| 2012/0255418 | A1* | 10/2012 | Hart | G10D 1/005 |
| | | | | 84/275 |
| 2018/0254023 | A1* | 9/2018 | Tsuruta | G10D 1/02 |
| 2019/0221194 | A1* | 7/2019 | Upton | G10D 1/02 |
| 2019/0325850 | A1* | 10/2019 | Soga | G10D 1/005 |
| 2019/0333482 | A1* | 10/2019 | Kazuki | G10D 1/005 |

FOREIGN PATENT DOCUMENTS

| | | |
|---|---|---|
| JP | 2001-124027 A | 5/2001 |
| JP | 2002-106525 A | 4/2002 |
| JP | 2006-126511 A | 5/2006 |

\* cited by examiner

ACOUSTIC STRING INSTRUMENT, AND METHODS FOR MANUFACTURING AND REPAIRING SAME

CROSS-REFERENCE TO RELATED APPLICATIONS

This application is a continuation application of International Application No. PCT/JP2017/001231, filed on Jan. 16, 2017. The entire disclosures of International Application No. PCT/JP2017/001231 are hereby incorporated herein by reference.

BACKGROUND

Technological Field

The present invention relates to an acoustic string instrument and methods for manufacturing and repairing same.

Background Information

Acoustic string instruments, such as violins, are often provided with a body between a top plate and a back plate. The top plate and the back plate have projections that project outwardly from the body. In the violin manufacturing process, a top plate and a back plate that are slightly larger than finished size are prepared. After the top plate and the back plate are fixed to the body, the outer peripheral edges of the top plate and the back plate are then processed along the body to adjust the width of the projections (refer to Chris Johnson "The Art of Violin Making," Robert Hale Ltd, April 1998). This violin manufacturing method is the traditional method of manufacturing violins that has been in continuous use for more than the past 400 years and requires proficient skill.

In the conventional manufacturing method, since the outer peripheral edges of the top plate and the back plate are trimmed after the top plate and the back plate are fixed to the body, a high-precision alignment of the top and back plates during fixing to the body is not required. However, the timbre of a violin changes as a function of the positional relationship between the body and the top plate and the positional relationship between the body and the back plate. As a result, a conventional violin has the problem of varying timbre.

This disclosure is made in view of these circumstances, and an object thereof is to provide an acoustic string instrument, and the like, which can simplify the manufacturing process and reduce the variability of the timbre.

SUMMARY

In order to solve the problem described above, an acoustic string instrument according to one embodiment of this disclosure comprises a top plate, a back plate, and a body disposed between the top plate and the back plate. The body has a plurality of first positioning portions. At least one of the top plate or the back plate, or both has a plurality of second positioning portions. The first positioning portions are fixed to the second positioning portions corresponding to the first positioning portions.

In addition, a method for manufacturing an acoustic string instrument according to one embodiment of this disclosure comprises forming a plurality of first holes on a body and forming a plurality of second holes, which have a one-to-one correspondence with the first holes, in a body-side surface of at least one of a top plate, or both, having an outer peripheral edge has been processed; inserting a dowel into each of the first holes on the body or into each of the plurality of second holes on the at least one of the top plate or the back plate; applying an adhesive to at least one of the body-side surface, or a surface of the body, or both; and fixing the body to the top plate or the back plate by inserting the dowel projecting from the second holes of the top plate or the back plate into the first holes of the body, or by inserting the dowel projecting from the first holes of the body into the second holes of the top plate or the back plate.

In addition, a method for repairing an acoustic string instrument according to one embodiment of this disclosure comprises separating a body having a plurality of first holes from a top plate or a back plate having a plurality of second holes having a one-to-one correspondence with the plurality of first holes; removing a plurality of dowels from the plurality of first holes of the body and form the plurality of second holes of the top plate or the back plate; repairing at least one or more of the body, the top plate, or the back plate; inserting a plurality of different dowels into the plurality of first holes of the body, or into the plurality of second holes of the top plate or the back plate; applying an adhesive to at least one of a body-side surface of the top plate or the back plate, or a surface of the body, of both; and fixing the body to the top plate or the back plate by inserting the plurality of different dowels projecting from the plurality of second holes of the top plate or the back plate into the plurality of first holes of the body, or by inserting the plurality of different dowels projecting from the plurality of first holes of the body into the plurality of second holes of the top plate or the back plate.

DETAILED DESCRIPTION OF THE EMBODIMENTS

Embodiments are described below with reference to the figures. Selected embodiments will now be explained with reference to the drawings. It will be apparent to those skilled in the field of musical instruments from this disclosure that the following descriptions of the embodiments are provided for illustration only and not for the purpose of limiting the invention as defined by the appended claims and their equivalents.

1. Overall Structure

In the following description, a violin 1 will be described as one example of an acoustic string instrument. The acoustic string instrument according to this disclosure can be a violin type acoustic bowed string instrument, such as cello, viola, or a double bass, or a plucked string instrument, such as guitar or mandolin.

Figure 1:
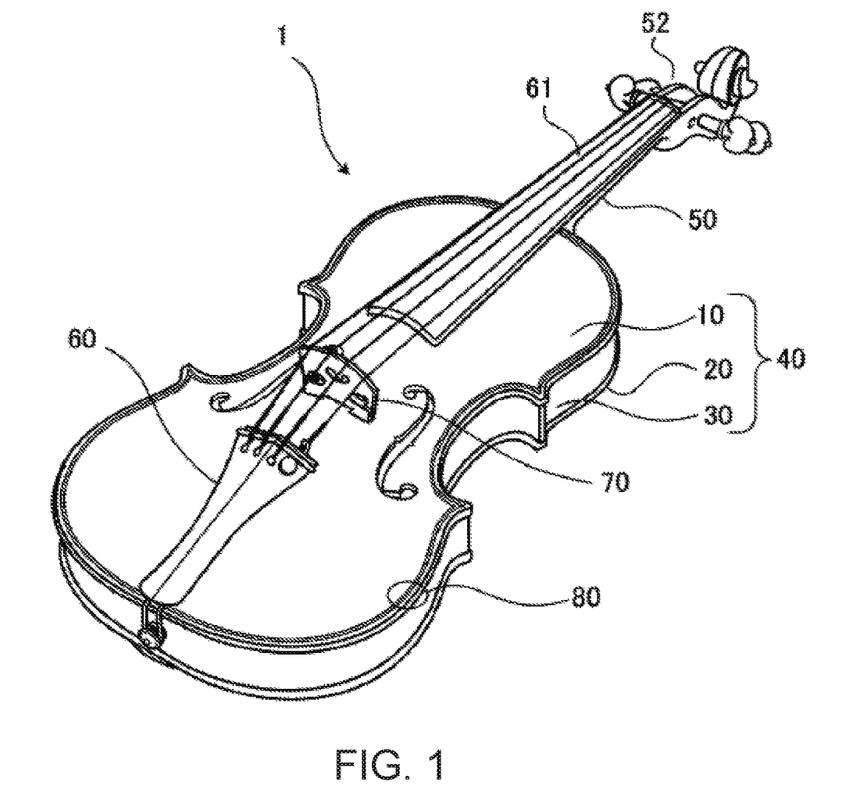
FIG. 1 is an external perspective view of a violin according to an embodiment.

FIG. 1 is an external perspective view of a violin according to an embodiment. The violin 1 comprises a main body 40 and a neck 50. The main body 40 includes a top plate 10, a back plate 20, and a body (rib) 30 provided between the top plate 10 and the back plate 20.

A tailpiece 60, a fingerboard 61, and a bridge 70 are provided on the top plate 10. One end of a string is fixed to the tailpiece 60, and the other end is fixed to a peg 52 provided at a distal end portion of the neck 50.

For example, a laminated plate is used for the top plate 10. The top plate 10 is formed by laminating a front faceplate, a back faceplate, and a core plate disposed therebetween with an adhesive. The materials of the front faceplate, the back faceplate, and the core plate can be the same or different. For example, spruce, maple, pine, cedar, birch, beech, or lauan can be used for these plates. It is particularly preferable to use spruce, which provides excellent vibration performance of the top plate 10. Moreover, it is preferable to configure the top plate 10 such that the front faceplate, the back faceplate, and the core plate are all made of spruce. By using spruce as the material for all of the front faceplate, the back faceplate, and the core plate, more excellent performance of the top plate 10 can be obtained, and the sound quality of the violin 1 can thereby be improved. In addition, in the top plate 10 of the present embodiment, a better appearance can be achieved by using straight-grained spruce for the front faceplate.

Figure 2:
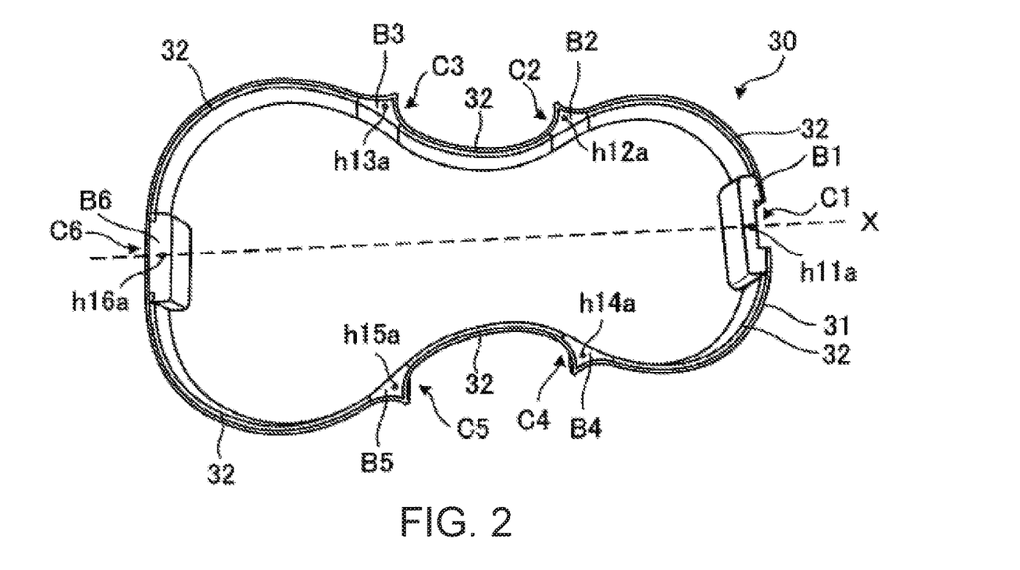
FIG. 2 is a perspective view illustrating a configuration of a body as seen from a top plate side.

Next, FIG. 2 is a perspective view illustrating a configuration of the body 30 as seen from the top plate side. The material of the body 30 is wood. The body 30 includes a side plate 31, six reinforcing plates 32, and six blocks B1-B6. The side plate 31 is a plate for the exterior, which forms a space (space for resonating the vibration that propagates from the strings) by surrounding the space between the top plate 10 and the back plate 20. The reinforcing plates 32 are fixed to the interior of the side plate 31. Portions where a reinforcing plate 32 is not fixed to the interior of the side plate 31 are called corners. In the example shown in FIG. 2, there are six corners C1-C6. Corners C2-C4 are positioned in portions where the side plate 31 forms an acute angle, corner C1 is positioned in a portion where the neck 50 is attached, and corner C6 is positioned at the bottom portion of the violin 1. Then, blocks B1-B6 are fixed to the side plate 31 so as to have a one-to-one correspondence with the six corners C1-C6.

In addition, first holes h11a-h16a are formed in the blocks B1-B6 as seen from the top plate side. The first holes h11a-h16a have a columnar shape, formed on the top plate side of the blocks B1-B6 with a prescribed depth toward the back plate side, but do not penetrate the blocks B1-B6. The first holes h11a-h16a are used for positioning the top plate 10 and the body 30 when the two are fixed to each other.

Figure 3:
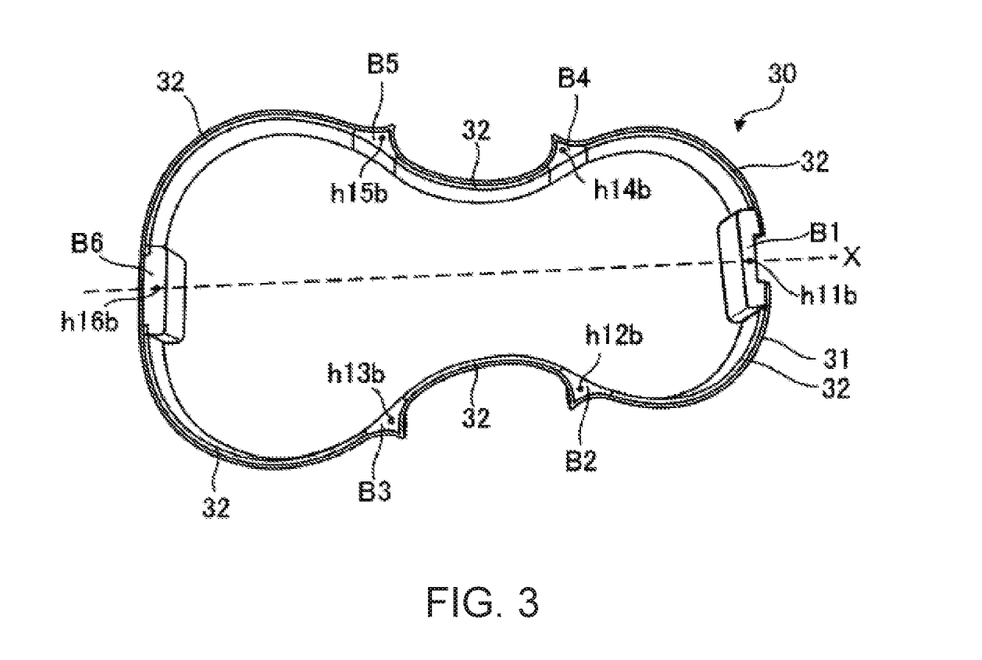
FIG. 3 is a perspective view illustrating the configuration of the body as seen from a back plate side.

FIG. 3 is a perspective view illustrating the configuration of the body 30 as seen from the back plate side. As shown in this figure, first holes h11a-h16b are formed in the blocks B1-B6 as seen from the back plate side. The first holes h11a-h16a have a columnar shape, formed on the back plate side of the blocks B1-B6 with a prescribed depth toward the top plate side, but do not penetrate the blocks B1-B6. The first holes h11a-h16a are used for positioning the back plate 20 and the body 30 when the two are fixed to each other.

Figure 4:
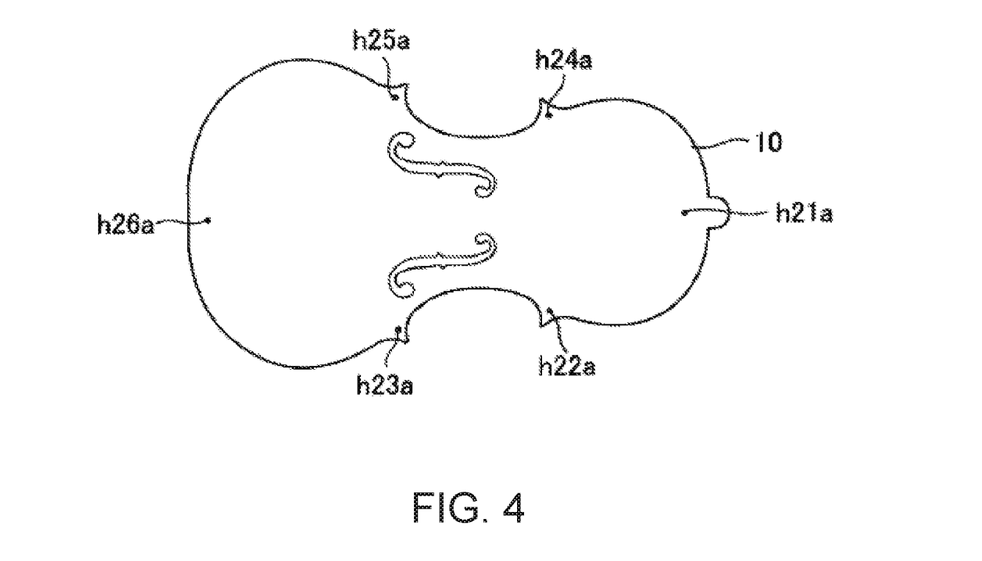
FIG. 4 is a plan view of the top plate as seen from the body side.
Figure 5:
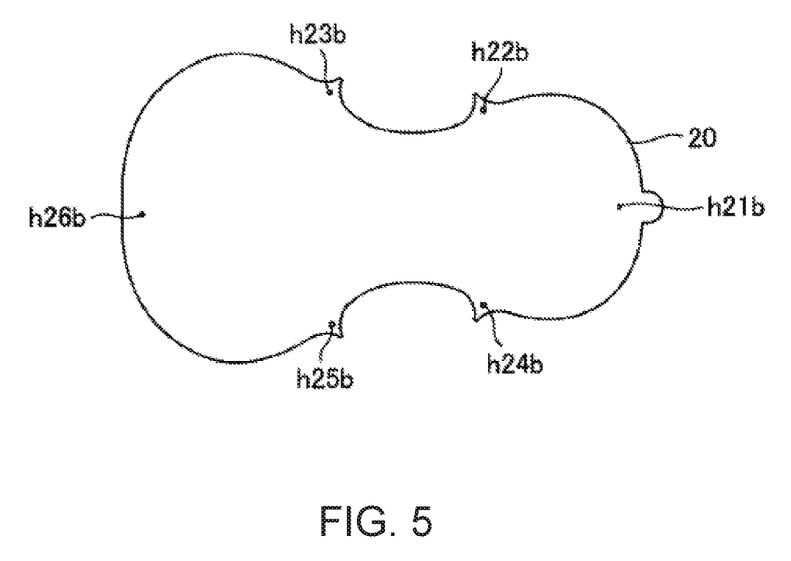
FIG. 5 is a plan view of the back plate as seen from the body side.

FIG. 4 is a plan view of the top plate 10 as seen from the body side. As illustrated in the figure, second holes h21a-h26a are formed in the top plate 10. FIG. 5 is a plan view of the back plate 20 as seen from the body side. As illustrated in the figure, second holes h21b-h26b are formed in the back plate 20.

The second holes h21a-h26a are formed in positions opposing the first holes h11a-h16a of the body 30 in a state in which the top plate 10 and the body 30 have an appropriate positional relationship. In addition, the second holes h21b-h26b are formed in positions opposing the first holes h11b-h16b of the body 30 in a state in which the back plate 20 and the body 30 have an appropriate positional relationship.

The back plate 20 and the body 30 are positioned using a plurality of fixing members. In the present embodiment, the plurality of fixing members are dowels. The dowel is a columnar member having the same cross-sectional shape (for example, circular) as the first holes h11a-h16a and h11b-h16b as well as the second holes h21a-h26a ad h21b-h26b.

Specifically, a dowel is inserted in each of the first holes h11b-h16b formed in the body 30. Next, the dowels projecting from the first holes h11b-h16b are respectively inserted in the second holes h21b-h26b of the back plate 20, and the body 30 and the back plate 20 are fixed with an adhesive.

Similarly, the dowels are also used to position the top plate 10 and the body 30. Specifically, a dowel is inserted in each of the first holes h11a-h16a formed in the body 30. Next, dowels projecting from the first holes h11a-h16a are respectively inserted in the second holes h21a-h26a of the top plate 10, and the body 30 and the top plate 10 are fixed with an adhesive. It will be apparent to those skilled in the art from this disclosure that the plurality of fixing members are not limited to the dowels. For example, other types of fasteners can be used as the fixing members.

Here, if the depth of the first holes forming a pair is L1, the depth of the second hole is L2, and the length of the dowel is L3, the following equations are established.

$$L1 < L3 \quad \text{Equation 1}$$

$$L2 < L3 \quad \text{Equation 2}$$

$$L1 + L2 > L3 \quad \text{Equation 3}$$

It can be seen from Equations 1 and 2 that whether the dowel is inserted in the first hole or the second hole, the dowel projects from the hole. It is possible to position the body 30 in the horizontal direction by means of these projecting portions.

The first holes h11a-h16a shown in FIG. 2 are arranged bilaterally symmetrically with respect to a longitudinal center line X of the body 30, and the first holes h11b-h16b shown in FIG. 3 are arranged bilaterally symmetrically with respect to the longitudinal center line X of the body 30. The first holes h11a, h16a, h11b, and h16b are positioned on the center line X. By arranging the first holes h11a-h16a and h11b-h16b dispersed in this manner, it is possible to position the body 30 and the top plate 10 with high precision and to position the body 30 and the back plate 20 with high precision.

Moreover, there are cases in which the top plate 10 and the back plate 20 are separated from the body 30 when repairing the violin 1. The dowels are used for positioning but do not contribute to the fixing of the body 30 and the top plate 10 or the fixing of the body 30 and the back plate 20. However, there are cases in which adhesive flows into the first hole or the second hole in the step to bond the body 30 and the top plate 10 and the step to bond the body 30 and the back plate 20. In such a case, when the dowels and the body 30, the dowels and the top plate 10, or the dowels and the back plate 20 are fixed by means of the adhesive, it becomes cumbersome to separate the top plate 10 and the back plate 20 from the body 30. Therefore, even if the adhesive flows between the dowels and the body 30, the bonding strength between the dowels and the body 30, between the dowels and the top plate 10, and between the dowels and the back plate 20 is preferably weak, such that the top plate 10 and the back plate 20 can be easily separated from the body 30.

In the present embodiment, the material of the body 30, the top plate 10, and the back plate 20 is wood. In addition, the material of the dowels is not particularly limited but is preferably resin or metal. If the material of the dowels is resin or metal and an adhesive used for woodworking is employed, even if the adhesive flows into the first holes or the second holes, the bonding strength between the dowels and the top plate 10, the back plate 20, and the body 30 is weak, so that repair becomes easy. Examples of such an adhesive include glue and vinyl acetate resin emulsion. Since the material of the dowels is selected from the standpoint of bonding strength, with consideration given to repair, it is sufficient if the surface of the dowels is resin or metal. That is, the dowel can be obtained by coating wood with resin, or by covering a columnar piece of wood with a cylindrical metal.

In general, the top plate and the back plate of a violin have peripheral portions that are thicker than the central portions. This is to increase the vibration of the top plate and the back plate. The vibration of a violin is classified into various modes, but the vibration in the direction perpendicular to the top plate and the back plate accounts for a large proportion of the overall vibration of the violin. In the present embodiment, a material other than wood can be used for the dowels. Alternatively, even if the material of the dowels is wood, it is possible to use a different type of wood than that used for the top plate 10, the back plate 20, and the body 30. Since the dowels are provided between the body 30 and the top plate 10 and the back plate 20, the longitudinal vibration can be adjusted according to at least one or more of the following: the dowel material, dowel length, or dowel diameter. For example, if rubber is employed as the dowel material, since rubber is softer than wood, it becomes easier to make the top plate 10 vibrate in the perpendicular direction. That is, by reducing the rigidity of the outer peripheral portion of the top plate 10, it becomes possible to improve the rising of the sound.

In this manner, in addition to the function of positioning the body 30 in relation to the top plate 10 and the back plate 20, the dowels have the function of adjusting the timbre of the violin 1. Therefore, compared with a conventional violin in which the top plate and the back plate are fixed to the body without using dowels, with the violin 1 according to the present embodiment, it is possible to increase the number of elements for adjusting the timbre.

Figure 6:
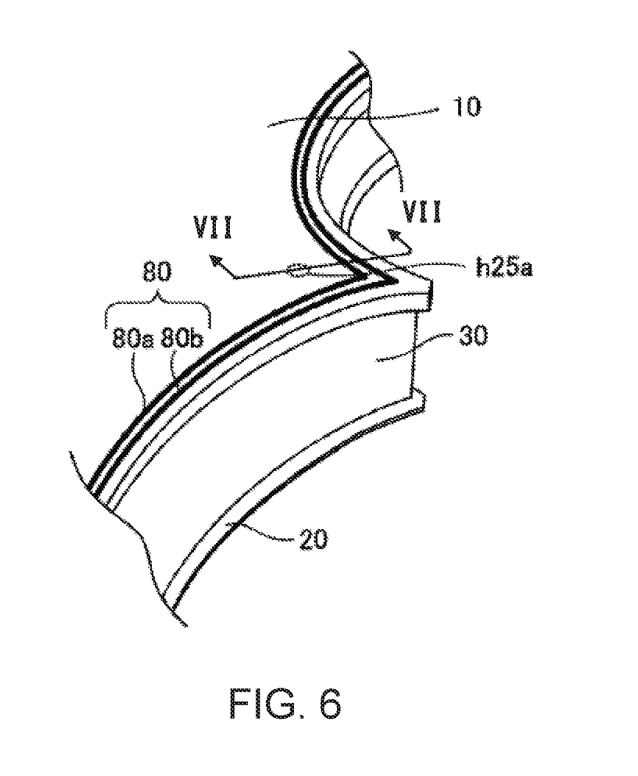
FIG. 6 is an enlarged perspective view illustrating a part of the violin.

Next, a purfling 80 is formed at the peripheral portions of the top plate 10 and the back plate 20. In addition to a design effect, the purfling 80 has the function of absorbing shock. The relationship between the purfling 80 and the second holes h21a-h26a and h21b-h26b will be described. FIG. 6 is an enlarged perspective view illustrating a part of the violin 1. The purfling 80 has two purfling lines 80a and 80b. The purfling line 80b is formed in the peripheral portion of the top plate 10, maintaining a set distance from the edge of the top plate 10. The same applies to the purfling line 80a.

Figure 7:
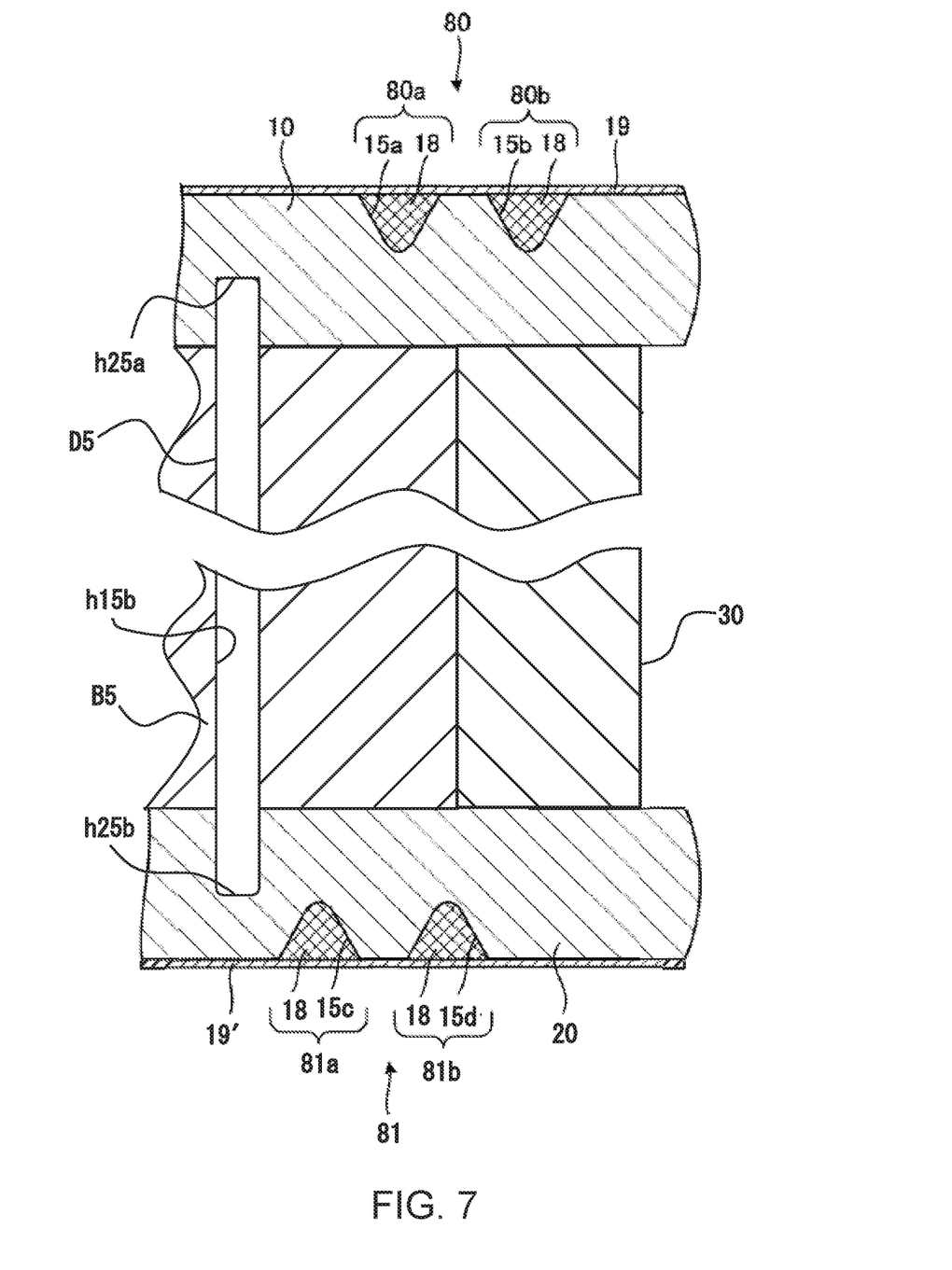
FIG. 7 is a cross-sectional perspective view illustrating a cross section of a portion of the violin as seen along the section line of FIG. 6.

FIG. 7 shows a cross section of the top plate 10 through the section line VII-VII of FIG. 6. As shown in FIG. 7, the purfling 80 is formed by embedding liquid resin 18 in a groove 15a and a groove 15b formed on the top plate 10, curing the resin 18 thereafter, and further providing a protective layer 19 on the top surface. The groove 15a and the groove 15b have an essentially V-shaped cross section, in which the bottom portion is rounded. More specifically, the grooves are composed of a first side surface and a second side surface, which are inclined with respect to the surface of the top plate 10, and a curved bottom portion. By rounding the bottom portion, it is possible to fill the groove 15a and the groove 15b with the resin 18 without gaps, even if the resin 18 has low fluidity and high viscosity. In addition, if the bottom portion were not rounded and had a sharp V shape, when the resin 18 thermally expands, a force in a direction perpendicular to the first side surface would act from the interior of the groove outwardly, and a force in a direction perpendicular to the second side surface would act from the interior of the groove outwardly. These forces generate stress that pulls in two directions, particularly in a portion where the first side surface and the second side surface come into contact. In contrast, since the bottom portion is rounded in the present embodiment, a force that is perpendicular to the curved surface acts at the bottom portion. Therefore, it is possible to reduce the generation of localized stress. The cross-sectional shape of the groove 15a and the groove 15b can also be rectangular, arcuate, or trapezoidal. In the illustrated embodiment, the back plate 20 has purfling 81 that is the same as the purfling 80 of the top plate 10 as shown in FIG. 7. Thus, the purfling 81 is formed by embedding the liquid resin 18 in a groove 15c and a groove 15d formed on the back plate 20, curing the resin 18 thereafter, and further providing a protective layer 19' on the outer surface.

Conventionally, a purfling is formed by embedding a member into a groove having a rectangular cross section using an inlay technique. Compared to conventional purfling, the purfling according to the present embodiment has the following benefits.

First, since it is only necessary to fill the groove 15a and the groove 15b with the resin 18, it is possible to easily manufacture the violin 1 without the reliance on inlaying skills. Second, since the resin 18 is softer than wood, shock can be absorbed by the purfling 80 when the body 30 of the violin 1 is struck against a wall, etc. Third, in the groove 15a and the groove 15b, it is possible to adjust the timbre of the violin 1 by adjusting at least one or more of the following: the depth, width, groove, or the viscosity of the resin.

Here, the second hole h25a of the top plate 10 is formed on the inner side of the purfling 80, as shown in FIGS. 6 and 7. Similarly, the other second holes h21a-h24a and h26a formed in the top plate 10 and the second holes h21b-h26b formed in the back plate 20 are also formed on the inner side of the purfling 80. In the top plate 10 and the back plate 20, the reason for providing the second holes h21a-h26a and h21b-h26b on the inner side of the purfling 80 is to suppress a reduction in strength. If the groove 15a and the groove 15b were to overlap the second holes h21a-h26a, when the top plate 10 is seen from a direction perpendicular to the surface, the thickness of the wood of the overlapped portion would be thinner, compared to a case in which the grooves and the holes do not overlap. As a result, the strength would be greatly reduced at said portion. In contrast, if the second holes h21a-h26a and h21b-h26b are formed on the inner side of the purfling 80, it is not necessary to make the thickness of the wood as thin, and it becomes possible to suppress a reduction in strength.

2. Method for Manufacturing the Violin

Figure 8:
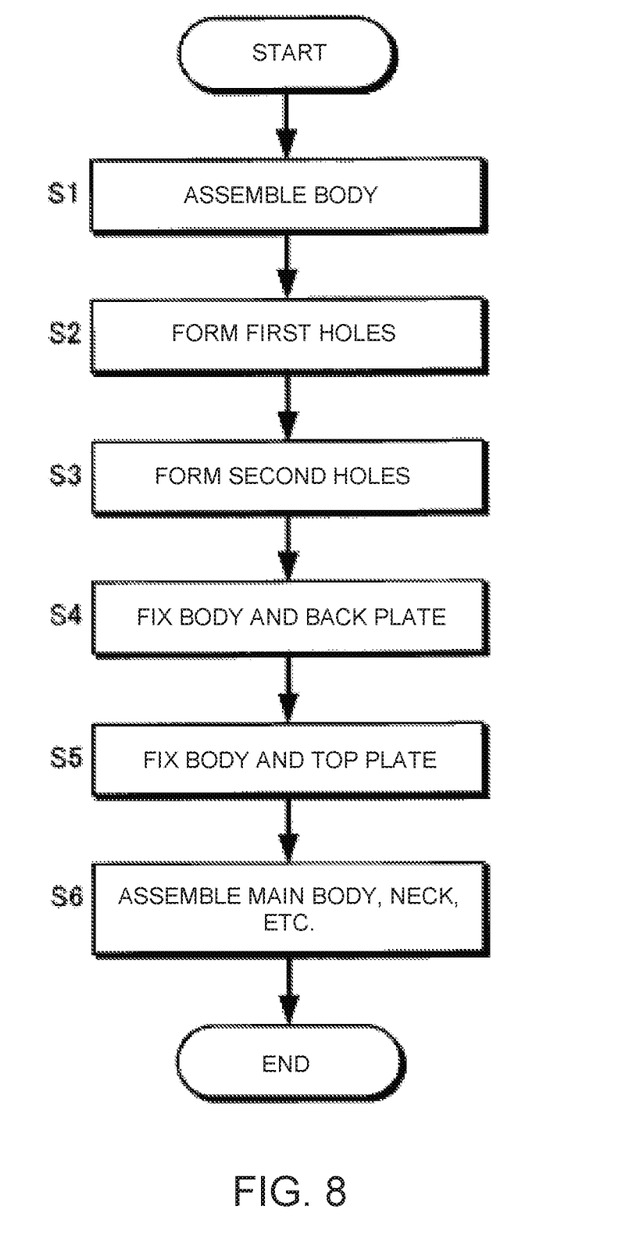
FIG. 8 is a flowchart illustrating a manufacturing process of the violin.

Next, the method for manufacturing the violin 1 will be described. FIG. 8 is a flowchart illustrating a manufacturing process of the violin 1.

Figure 9:
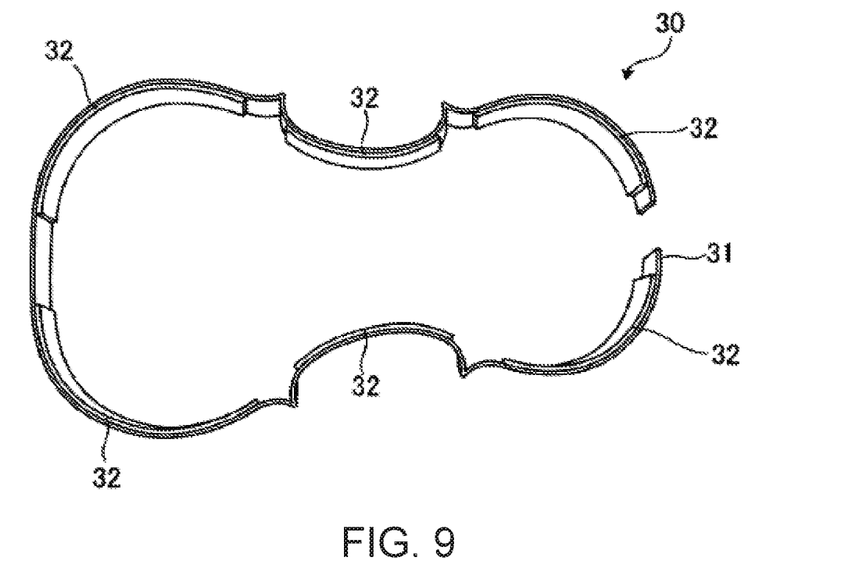
FIG. 9 is a perspective view illustrating a mode in which a side plate and six reinforcing plates are fixed to each other.
Figure 10:
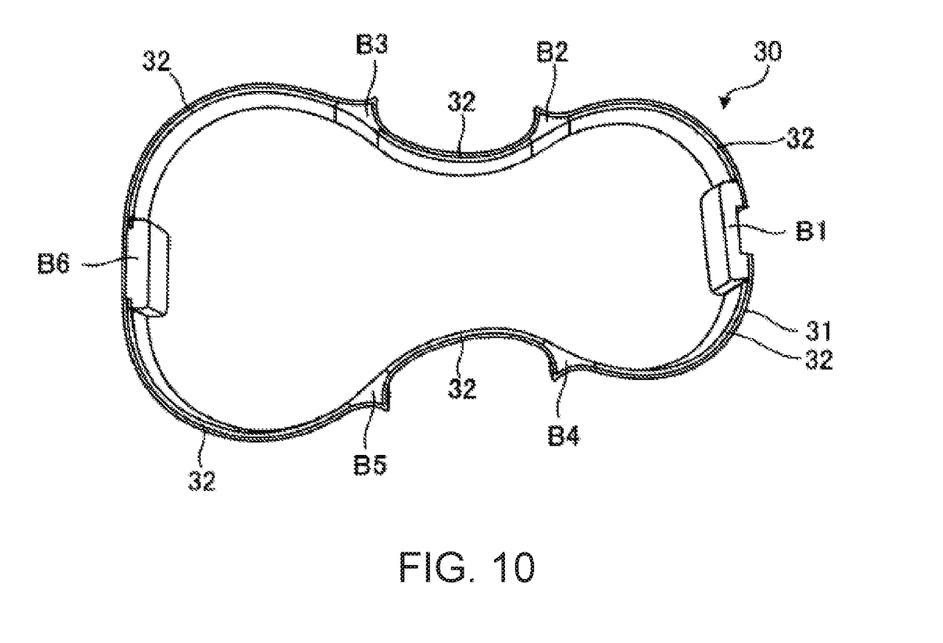
FIG. 10 is a perspective view illustrating a body to which are added six blocks.

First, in the first step, the body 30 is assembled (S1). Specifically, as shown in FIG. 9, the side plate 31 and the six reinforcing plates 32 are fixed by using an adhesive. Thereafter, the blocks B1-B6 are fixed to each corner of the side plate 31 by using an adhesive to form the body 30 shown in FIG. 10. The body 30 is strengthened by the addition of the blocks B1-B6.

Then, in the second step, the first holes h11a-h16a and h11b-h16b are formed in the body 30 (S2). Specifically, the first holes h11a-h16a for attaching the top plate 10 to each of the blocks B1-B6 are formed. As a result, the body 30, as seen from the top plate side, takes on the appearance shown in FIG. 2.

In addition, the first holes h11b-h16b for attaching the back plate 20 to each of the blocks B1-B6 are formed. As a result, the body 30, as seen from the back plate side, takes on the appearance shown in FIG. 3.

The first holes h11a-h16a function as a plurality of first positioning portions for positioning the top plate 10 to the body 30, and the first holes h11b-h16b function as a plurality of first positioning portions for positioning the back plate 20 to the body 30.

Therefore, it is preferable to form the first holes h11a-h16a and h11b-h16b at accurate positions using a machine tool for cutting that employs NC control (Numerical Control).

Then, in the third step, the second holes h21a-h26a for connecting the body 30 to the body-side surface of the top plate 10 are formed, and the second holes h21b-h26b for connecting the body 30 to the body-side surface of the back plate 20 are formed (S3). As a result, the top plate 10, as seen from the body side, takes on the appearance shown in FIG. 4, and the back plate 20, as seen from the body side, takes on the appearance shown in FIG. 5.

The outer peripheral edges of the top plate 10 and the back plate 20 are already processed into the completed forms. That is, in the present embodiment, the outer peripheral edges of the top plate 10 and the back plate 20 are not processed after fixing the top plate 10 and the back plate 20 to the body 30 as in the prior art. The top plate 10 and the back plate 20, whose edges have been shaped, are prepared in advance, and are positioned and fixed to the body 30 with high precision.

The second holes h21a-h26a function as a plurality of second positioning portions for positioning the top plate 10 with respect to the body 30, and the second holes h21b-h26b function as a plurality of second positioning portions for positioning the back plate 20 with respect to the body 30.

Therefore, it is preferable to form the second holes h21a-h26a and h21b-h26b at accurate positions using a machine tool for cutting that employs NC control.

Figure 11:
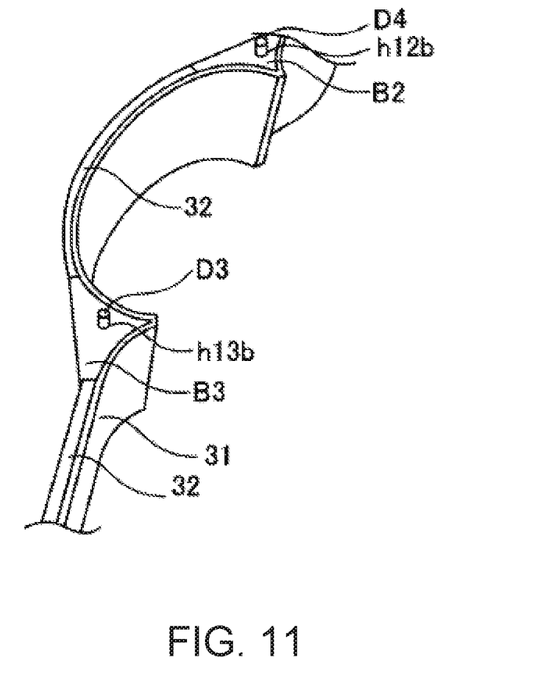
FIG. 11 is a perspective view illustrating a state in which dowels are inserted in the blocks.
Figure 12:
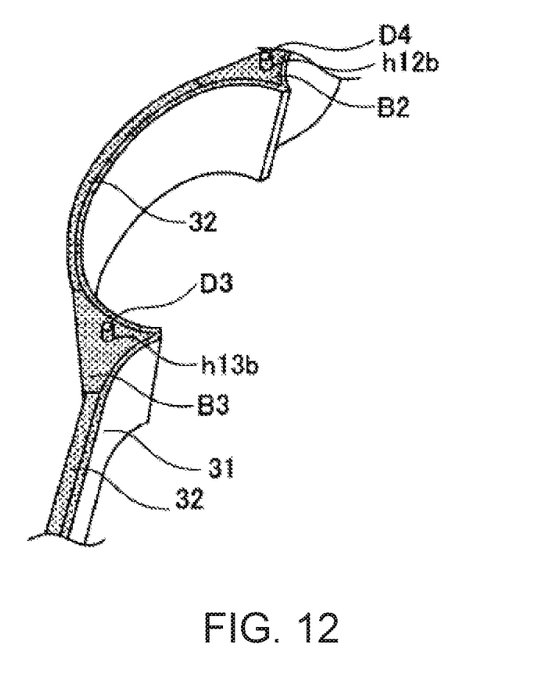
FIG. 12 is a perspective view illustrating the body to which an adhesive is applied.
Figure 13:
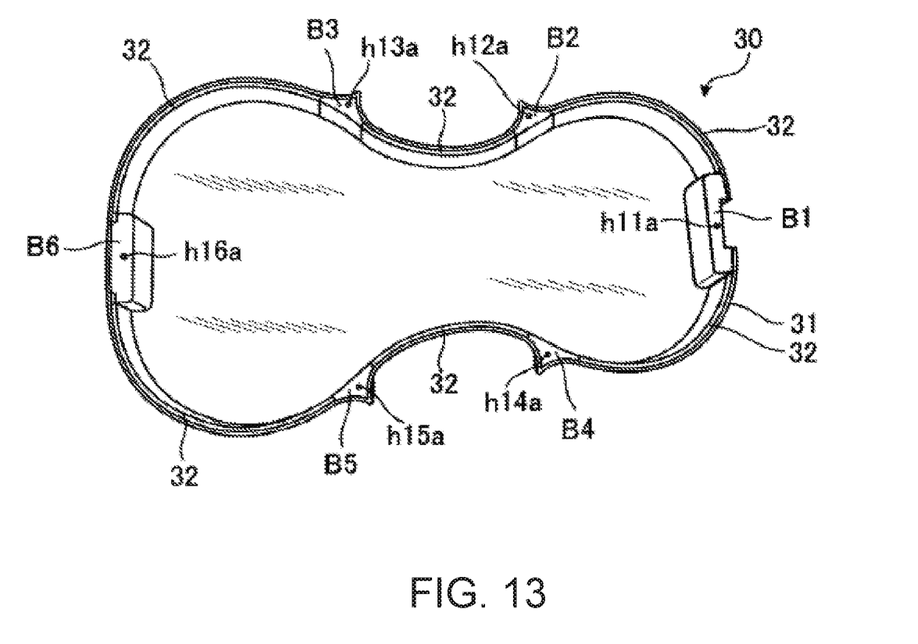
FIG. 13 is a perspective view of the body to which the back plate is fixed, as seen from the top plate side.

Then, in the fourth step, the body 30 and the back plate 20 are fixed (S4). First, a dowel is inserted into each of the first holes h11b-h16b of the blocks B1-B6. FIG. 7 shows a state in which dowel D5 is inserted into the block B5. FIG. 11 shows a state in which dowels D2 and D3 are respectively inserted into the blocks B2 and B3. Because the length of the dowel D3 is longer than the depth of the first hole h13b, the dowel D3 projects from the first hole h13b. Furthermore, the length of the portion projecting from the first hole h13b is slightly shorter than the depth of the second hole h23b formed in the back plate 20. Then, an adhesive such as glue is applied to the surface of the body 30 opposing the back plate 20. FIG. 12 shows the body 30 on which the adhesive is applied. The adhesive that adheres to the dowel is preferably wiped off. Alternatively, the adhesive can be applied after placing a cap on the dowel, and the cap can be removed afterward. Then, each dowel is inserted into the second holes h21b-h26b of the back plate 20, and the back plate 20 and the body 30 are fixed to each other. FIG. 13 shows the body 30 to which the back plate 20 is fixed, as seen from the top plate side.

Then, in the fifth step, the body 30 and the top plate 10 are fixed (S5). First, a dowel is inserted into each of the first holes h11a-h16a of the blocks B1-B6. Thereafter, an adhesive, such as glue, is applied to the surface of the body 30 to which the top plate 10 is fixed, in the same manner as in the fourth step. Each dowel is inserted into the second holes h21a-h26a of the top plate 10, and the top plate 10 and the body 30 are fixed to each other. The point that consideration is given so that the adhesive does not adhere to the dowels is the same as in the fifth step.

Then, in the sixth step, the main body 40, the neck 50, and the like are assembled (S6). Specifically, the neck 50 is attached to the main body 40 such that an attachment portion of the neck 50 is fitted into a recess of the block B1. Then, the fingerboard 61, the tailpiece 60, and the bridge 70 are attached to the main body 40.

By means of the manufacturing method described above, the top plate 10 and the back plate 20 can be positioned and fixed to the body 30 with high accuracy. As a result, it is possible to make the timbre almost uniform when mass-producing violins. In addition, it is not necessary to shape the end portions of the top plate 10 and the back plate 20 after fixing. As a result, it is possible to shorten the production time and to manufacture a violin without proficient skills.

3. Method for Repairing the Violin

Figure 14:
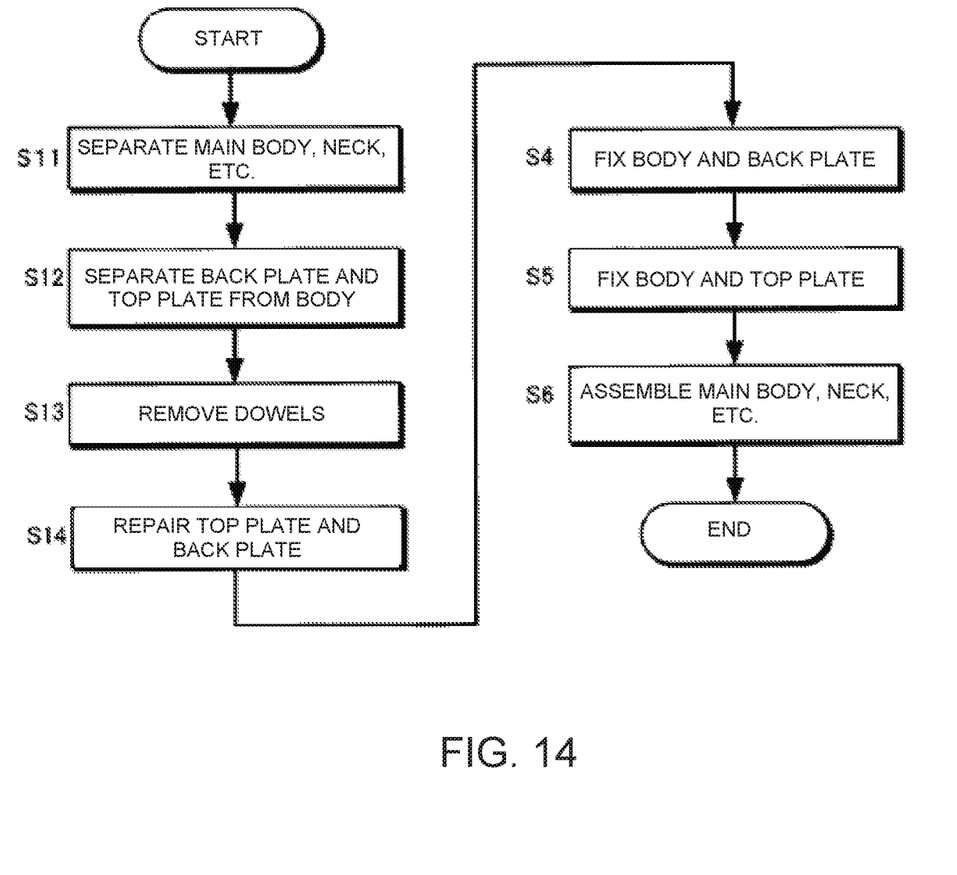
FIG. 14 is a flowchart illustrating a repair process of the violin.

Next, the method for repairing the violin 1 will be described. FIG. 14 is a flowchart illustrating a repair process of the violin 1.

First, in the first step, the main body 40 and the neck 50 are separated (S11). Specifically, in addition to the neck 50, parts attached to the main body 40, such as the fingerboard 61, the tailpiece 60, and the bridge 70, are separated from the main body 40.

In the second step, at least one of the back plate 20, the top plate 10, or both is separated from the body 30 (S12). For example, in the case that the adhesive bonding the body 30 to the back plate 20 and the top plate 10 is glue, a chisel is driven into the bonding surface while the violin 1 is heated to separate the back plate 20 and the top plate 10 from the body 30. Thereafter, the adhesive that remains on the body 30, the back plate 20, and the top plate 10 is removed.

In the third step, the dowels are removed from the first holes h11$a$-h16$a$ and h11$b$-h16$b$ and the second holes h21$a$-h26$a$ and h21$b$-h26$b$ (S13).

In the fourth step, at least one or more of the back plate 20, the top plate 10, or the body 30 is repaired (S14). For example, maintenance such as re-erecting the sound post inside the body 30 is carried out. Moreover, it is not necessary to repair both the back plate 20 and the top plate 10; either of the two can be repaired.

The fourth to the sixth steps (S4-S6) of the method for repairing the violin 1 in FIG. 14 are the same as the fourth to the sixth steps (S4-S6 in FIG. 8) of the method for manufacturing the violin 1 described above; thus, the detail descriptions thereof are omitted. In fourth and fifth steps of the method for repairing the violin 1, a plurality of dowels (a plurality of different dowels) inserted into the first holes h11$a$-h16$a$ and h11$b$-h16$b$ and the second holes h21$a$-h26$a$ and h21$b$-h26$b$ are different from the dowels removed from the first holes h11$a$-h16$a$ and h11$b$-h16$b$ and the second holes h21$a$-h26$a$ and h21$b$-h26$b$ in the third step (S13).

By means of the repair method described above, since the first holes h11$a$-h16$a$ and h11$b$-h16$b$, the second holes h21$a$-h26$a$ and h21$b$-h26$b$, and the dowels are used, it is possible to position the top plate 10 and the back plate 20 with the body 30 with high precision at the time of reassembly. As a result, the timbre of the violin after the repair can be kept close to that before the repair.

4. Modified Examples

The disclosure is not limited to the embodiment described above, and various modifications such as the following are possible. One or a plurality of the embodiments described above and the modified embodiments described below can be arbitrarily selected and appropriately combined.

(1) In the embodiment described above, the violin 1 is used as one example of an acoustic string instrument, but this disclosure is not limited thereto, and can be applied to any instrument provided with a body, a top plate and the back plate, and a back plate. Examples of such instruments include acoustic string instruments, such as jazz guitars and classical guitars, which have an arched top.

(2) In the embodiment described above, the first holes h11$a$-h16$a$ are formed in the body 30 as first positioning portions for positioning the top plate 10 with respect to the body 30, and the first holes h11$b$-h16$b$ are formed in the body 30 as first positioning portions for positioning the back plate 20 with respect to the body 30. In addition, the second holes h21$a$-h26$a$ are formed in the top plate 10 as second positioning portions for positioning the top plate 10 and the body 30, and the second holes h21$b$-h26$b$ are formed in the back plate 20 as second positioning portions for positioning the back plate 20 with respect to the body 30.

The first positioning portions of this disclosure are not limited to the first holes, and the second positioning portions of this disclosure are not limited to the second holes. The first positioning portions and the second positioning portions can be any type of element that can define the relative positions of the top plate 10 and the back plate 20 with respect to the body 30.

Figure 15:
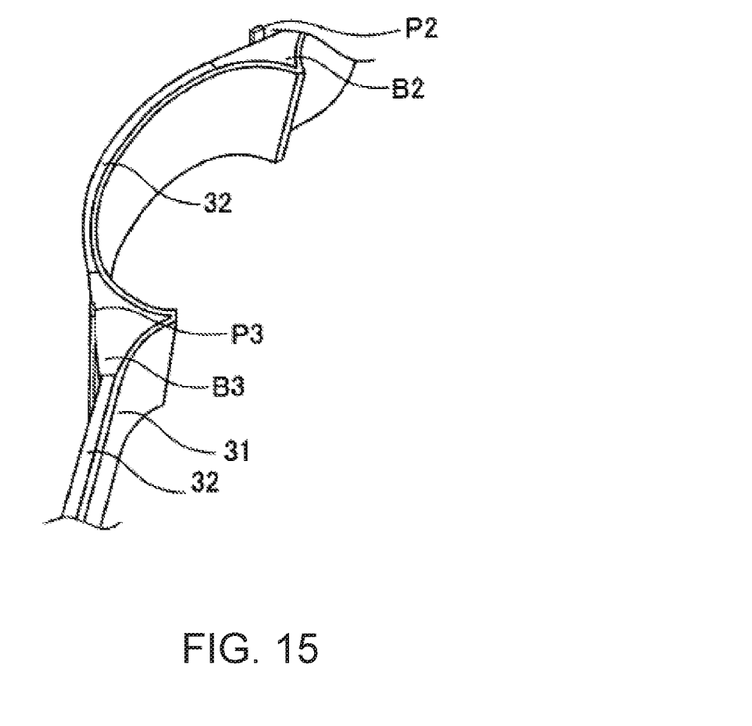
FIG. 15 is a positioning portion illustrating a specific example of a first positioning portion according to a modified example.

For example, as shown in FIG. 15, first positioning portions P2 and P3 can be respectively provided in the blocks B2 and B3 of the body 30. The first positioning portions P2 and P3 have a plate shape. The first positioning portions P2 and P3 are fixed to the inner side surface of the body 30 in the blocks B2 and B3 using an adhesive. In addition, the other blocks B1, B4, B5, and B6 are also provided with first positioning portions P1, P4, P5, and P6, in the same manner as the blocks B2 and B3.

Figure 16:
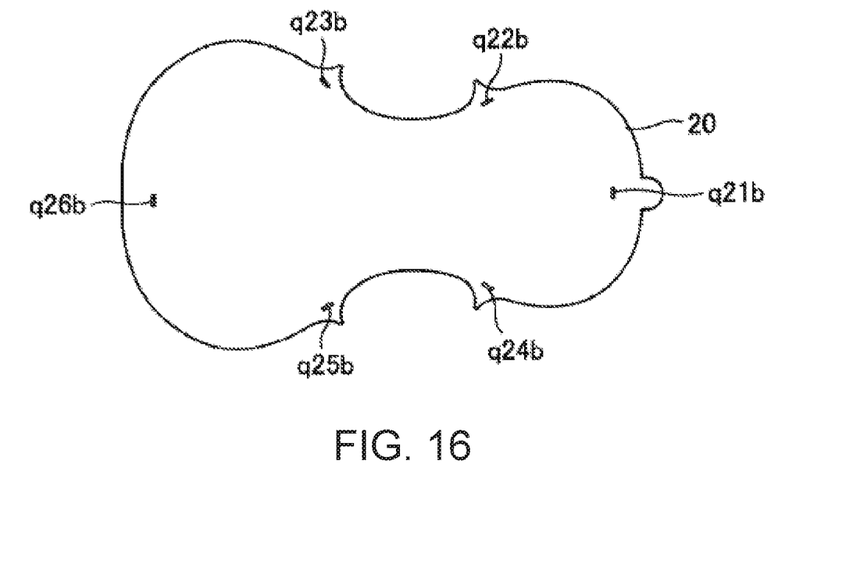
FIG. 16 is a plan view of a back plate as seen from the body side according to the modified example.

In addition, as shown in FIG. 16, the back plate 20 is provided with second holes q21$b$-q26$b$ into which the first positioning portions P1-P6 are inserted. In the embodiment described above, the planar shape of the second holes h21$b$-h26$b$ is circular, whereas the planar shape of the second holes q21$b$-q26$b$ of the modified example is rectangular. The second holes q21$b$-q26$b$ function as second positioning portions used for positioning the body 30 and the back plate 20. Since the relationship between the top plate 10 and the body 30 is the same, a description thereof is omitted.

(3) In the embodiment described above, the body 30 is provided with the first holes h11$a$-h16$a$ and h11$b$-h16$b$ as the first positioning portions, but this disclosure is not limited thereto; either the h11$a$-h16$a$ or the first holes h11$b$-h16$b$ can be provided as the first positioning portions. If the body 30 is provided with the first holes h11$a$-h16$a$ and not with the first holes h11$b$-h16$b$, the top plate 10 and the body 30 are positioned using the first holes h11$a$-h16$a$, the second holes h21$a$-h26$a$, and the six dowels, whereas the back plate 20 and the body 30 are not positioned using the dowels. Similarly, if the body 30 is provided with the first holes h11$b$-h16$b$ and not with the first holes h11$a$-h16$a$, the back plate 20 and the body 30 are positioned using the first holes h11$b$-h16$b$, the second holes h21$b$-h26$b$, and the six dowels, whereas the top plate 10 and the body 30 are not positioned using the dowels. That is, in the violin according to the modified example, the body 30 has a plurality of first holes serving as a plurality of first positioning portions for positioning the top plate 10 and/or the back plate 20 to the body 30, and the top plate 10 and/or the back plate 20 can be provided with a plurality of second holes serving as a plurality of second positioning portions that are provided in a one-to-one correspondence with the plurality of first positioning portions.

(4) In the embodiment described above, in the method for manufacturing a violin, the first holes h11$a$-h16$a$ and h11$b$-h16$b$ are formed in the second step, and the second holes h21$a$-h26$a$ and h21$b$-h26$b$ are formed in the third step, but the order thereof can be reversed, or the two steps can be performed in parallel.

Moreover, the fourth step and the fifth step can be reversed, or the two fixing steps can be performed in parallel.

In addition, in the fourth step, the adhesive is applied to the body 30, but this disclosure is not limited thereto; it is sufficient to apply the adhesive to the body-side surface of the top plate 10 and/or the top-plate-side surface of the body 30. Similarly, in the fifth step, the adhesive is applied to the body 30, but this disclosure is not limited thereto; it is sufficient to apply the adhesive to the body-side surface of the back plate 20 and/or the back-plate-side surface of the body 30.

In addition, in the fourth step, dowels are inserted into the first holes h11b-h16b of the body 30, and the back plate 20 is positioned by means of the six dowels that project from the first holes h11b-h16b, but this disclosure is not limited thereto. That is, dowels can be inserted into the second holes h21b-h26b of the back plate 20, and the body 30 can be positioned by means of the six dowels that project from the second holes h21b-h26b.

Similarly, in the fifth step, dowels are inserted into the first holes h21a-h16a of the body 30, and the top plate 10 is positioned by means of the six dowels that project from the first holes h11a-h16a, but this disclosure is not limited thereto. That is, dowels can be inserted into the second holes h21a-h26a of the top plate 10, and the body 30 can be positioned by means of the six dowels that project from the second holes h21a-h26a.

These modifications can of course be applied not only to the method for manufacturing a violin, but also to the method for repairing a violin.

(5) In the embodiment described above, the top plate 10 and the back plate 20 are made of laminated wood, but this disclosure is not limited thereto the top plate 10 and the back plate 20 can be made using any type of material. For example, the top plate 10 and/or the back plate 20 can be made using a single panel. In addition, fiberboard or a high-pressure laminate can be used.

Furthermore, non-wood materials can be used for the top plate 10 and the back plate 20. For example, carbon fiber or fiber glass can be used.

(6) In the embodiment described above, the purfling is composed of resin-filled grooves, but this disclosure is not limited thereto; the purfling can be formed by embedding a member into a groove having a rectangular cross section using an inlay technique.

(7) In the embodiment described above, the first holes h11a-h16a and h11b-h16b are used as one example of the plurality of first holes, but this disclosure is not limited thereto; it is sufficient to provide two or more first holes. Three or more first holes are preferably provided from the standpoint of improving positioning accuracy. In this case, the plurality of first holes arranged on the top plate 10 side of the body 30 preferably include a hole (for example, h12a or h13a) positioned on the left side (first side) of the longitudinal center line X of the body 30, a hole (for example, h14a or h15a) positioned on the right side (second side) of the longitudinal center line of the body, and a hole (for example, h11a or h16a) that is not arranged on a straight line that connects the centers of these holes. By means of this modified example, since the plurality of first holes include a hole positioned on the left side of the center line X and a hole positioned on the right side of the center line, the first holes will not be biased only to the left side or only to the right side of the longitudinal direction of the body 30. In addition, since all of the first holes will not be arranged in a straight line, it is possible to carry out positioning on a plane. Therefore, it is possible to improve the positioning accuracy between the top plate 10 and the body 30. Moreover, the positioning accuracy between the body 30 and the back plate 20 can be improved by arranging the first holes provided on the back plate 20 side of the body 30 in the same manner as the first holes on the top plate 10 side.

The following inventions can be understood from the embodiment and the modified examples described above.

A top plate, a back plate, and a body sandwiched between the top plate and the back plate are provided, wherein the body has a plurality of first positioning portions for positioning the top plate and/or the back plate on the body; the top plate and/or the back plate is provided with a plurality of second positioning portions having a one-to-one correspondence with the plurality of first positioning portions; and the plurality of first positioning portions are connected to the plurality of second positioning portions, which have a one-to-one correspondence therewith.

By means of this aspect of the acoustic string instrument, since positioning is carried out using the plurality of first positioning portions of the body and the plurality of second positioning portions provided in the top plate and/or the back plate, it is possible to fix the top plate and/or the back plate to the body easily and with high accuracy. As a result, it becomes a simple matter to manufacture acoustic string instruments with little variation in timbre.

In one aspect of the acoustic string instrument described above, preferably, the plurality of first positioning portions are the plurality of first holes formed in the body, the plurality of second positioning portions are the plurality of second holes provided in the top plate and/or the back plate, the plurality of first holes have a one-to-one correspondence with the plurality of second holes, and a plurality of dowels are provided for insertion into each of a pair of first holes and second holes.

By means of this aspect, since dowels can be used when positioning the top plate and/or the back plate with respect to the body, positioning can be easily carried out. In addition, the acoustic characteristics of the acoustic string instrument change in accordance with how the top plate and/or the back plate is connected to the body. The vibration of the top plate and/or the back plate can be adjusted by means of at least one or more of the following: the depths of the first holes and the second holes, the shape of the dowels, or the dowel material. Therefore, in addition to the positioning function, the dowels can have the function of adjusting the timbre of the acoustic string instrument.

In one aspect of the acoustic string instrument described above, the plurality of first holes are preferably arranged bilaterally symmetrically with respect to the longitudinal center line of the body. By means of this aspect, since the plurality of first holes are arranged bilaterally symmetrically, it is possible to increase the positioning accuracy.

In one aspect of the acoustic string instrument described above, the plurality of first holes preferably include a hole positioned on the left side of the longitudinal center line of the body, a hole positioned on the right side of the longitudinal center line of the body, and a hole that is not arranged on a straight line that connects the centers of these holes. By means of this modified example, since the plurality of first holes include a hole positioned on the left side of the center line and a hole positioned on the right side of the center line, the holes will not be biased only to the left side or only to the right side of the longitudinal direction of the body. In addition, since all of the holes will not be arranged in a straight line, it is possible to carry out the positioning on a plane. Therefore, it is possible to improve the positioning accuracy.

In one aspect of the acoustic string instrument described above, preferably, the top plate, the back plate, and the body are made of wood, and the surfaces of the plurality of dowels are made of resin or metal. By means of this aspect, because the bonding strength can be weakened by using an adhesive suitable for woodworking, even if the adhesive flows into the first holes and the second holes, the top plate and the back plate can be easily separated from the body at the time of repair.

In one aspect of the acoustic string instrument described above, preferably, a purfling is provided on the outer peripheral portion of the top plate and/or the back plate, and the plurality of second holes are formed on the inner side of the purfling.

By means of this aspect, since the second holes are formed on the inner side of the purfling, the groove of the purfling and the second holes will not be formed so as to overlap. Therefore, it is possible to maintain the strength of the top plate and/or the back plate. Here, the purfling preferably comprises a resin-filled groove. In this case, manufacture becomes easier compared to a purfling that is produced by means of an inlay technique. In addition, since shock can be absorbed by the resin, the impact resistance can be enhanced. Furthermore, the vibration of the top plate and/or the back plate can be adjusted by means of at least one or more of the following: the groove depth, the groove width, or the resin material. It thereby becomes possible to adjust the timbre of the acoustic string instrument.

One aspect of the method for manufacturing an acoustic string instrument is understood from the above-described embodiment and modified examples. The method comprises a step for forming a plurality of first holes on a body and forming a plurality of second holes, which have a one-to-one correspondence with the plurality of first holes, on a body-side surface of a top plate whose outer peripheral edge has been processed, or of a back plate whose outer peripheral edge has been processed; a step for inserting a dowel into each of the plurality of first holes on the body or into each of the plurality of second holes on the top plate or the back plate; a step for applying an adhesive to the body-side surface of the top plate or the back plate and/or a surface of the body; and a step for fixing the body to the top plate or the back plate by inserting a plurality of dowels projecting from the plurality of second holes of the top plate or the back plate into the plurality of first holes of the body, or by inserting a plurality of dowels projecting from the plurality of first holes of the body into the plurality of second holes of the top plate or the back plate.

By means of this one aspect of the manufacturing method, it is possible to fix the body with the top plate or the back plate easily and with high accuracy. As a result, it becomes a simple matter to manufacture acoustic string instruments with little variation in timbre.

One aspect of the method for repairing an acoustic string instrument is understood from the above-described embodiment and modified examples. Such a method for repairing an acoustic string instrument comprises a step for separating a body having a plurality of first holes from a top plate or a back plate having a plurality of second holes having a one-to-one correspondence with the plurality of first holes; a step for removing a plurality of dowels from the plurality of first holes of the body and from the plurality of second holes of the top plate or the back plate; a step for repairing the body, the top plate, or the back plate, a step for inserting a plurality of dowels into the plurality of first holes of the body, or into the plurality of second holes of the top plate or the back plate; a step for applying an adhesive to the body-side surface of the top plate or the back plate and/or a surface of the body; and a step for fixing the body to the top plate or the back plate by inserting a plurality of dowels projecting from the plurality of second holes of the top plate or the back plate into the plurality of first holes of the body, or by inserting a plurality of dowels projecting from the plurality of first holes of the body into the plurality of second holes of the top plate or the back plate.

By means of this one aspect of the repair method, it is possible to fix the body to the top plate or the back plate easily and with high accuracy. As a result, the timbre of the acoustic string instrument after the repair can be kept close to that before the repair.

What is claimed is:

1. An acoustic string instrument comprising:
   a top plate;
   a back plate;
   a body disposed between the top plate and the back plate and having a plurality of holes; and
   a plurality of fixing members connecting the body to at least one of the top plate or the back plate, or both;
   the at least one of the top plate or the back plate, or both having a plurality of blind holes on a body-side surface of the at least one of the top plate or the bottom plate, or both, the blind holes corresponding to the holes of the body, respectively,
   each of the plurality of fixing members contacting each of the holes of the body and each of the blind holes.

2. The acoustic string instrument according claim 1, wherein
   each of the fixing members is a dowel, which is disposed in each of the holes of the body and each of the blind holes.

3. The acoustic string instrument according to claim 1, wherein
   the holes of the body are arranged bilaterally symmetrically with respect to a longitudinal center line of the body.

4. The acoustic string instrument according to claim 1, wherein
   one of the holes of the body is positioned on a first side of a longitudinal center line of the body, one of the holes of the body is positioned on a second side of the longitudinal center line of the body, one of the holes of the body is positioned not on a straight line that connects centers of the hole positioned on the first side and the hole positioned on the second side, and the first side is opposite to the second side.

5. The acoustic string instrument according to claim 2, wherein
   the top plate, the back plate, and the body are made of wood, and
   surfaces of the plurality of dowels are made of resin or metal.

6. The acoustic string instrument according to claim 1, wherein
   at least one of the top plate or the back plate, or both further has a purfling disposed on an outer peripheral portion, and
   the blind holes are formed on an inner side of the purfling.

7. A method for manufacturing an acoustic string instrument, the method comprising:
   forming a plurality of holes on a body;
   forming a plurality of blind holes which have a one-to-one correspondence with the holes of the body, on a body-side surface of at least one of a top plate or a bottom plate, or both, the at least one of the top plate or the bottom plate, or both having an outer peripheral edge that has been processed;
   inserting a dowel into each of the holes of the body or into each of the blind holes;
   applying an adhesive to at least one of the body-side surfaces or a surface of the body, or both; and
   fixing the body to the at least one of the top plate or the back plate, or both by inserting the dowel projecting from the blind holes into the holes of the body, or by inserting the dowel projecting from the holes of the body into the blind holes.

8. A method for repairing an acoustic string instrument, the method comprising:
- separating a body having a plurality of holes from at least one of a top plate or a back plate, or both having a plurality of blind holes, which have a one-to-one correspondence with the holes of the body and are formed on a body-side surface of the at least one of the top plate or the back plate, or both;
- removing a plurality of dowels inserted into the holes of the body and the blind holes;
- repairing at least one or more of the body, the top plate, or the back plate;
- inserting a plurality of different dowels into the holes of the body, or into the blind holes;
- applying an adhesive to at least one of the body-side surfaces or a surface of the body, or both; and
- fixing the body to the at least one of the top plate or the back plate, or both by inserting the different dowels projecting from the blind holes into the holes of the body, or by inserting the different dowels projecting from the holes of the body into the blind holes.

* * * * *